Oct. 7, 1947. O. R. MEYER Plant Pat. 764
CHERRY TREE
Filed April 18, 1946
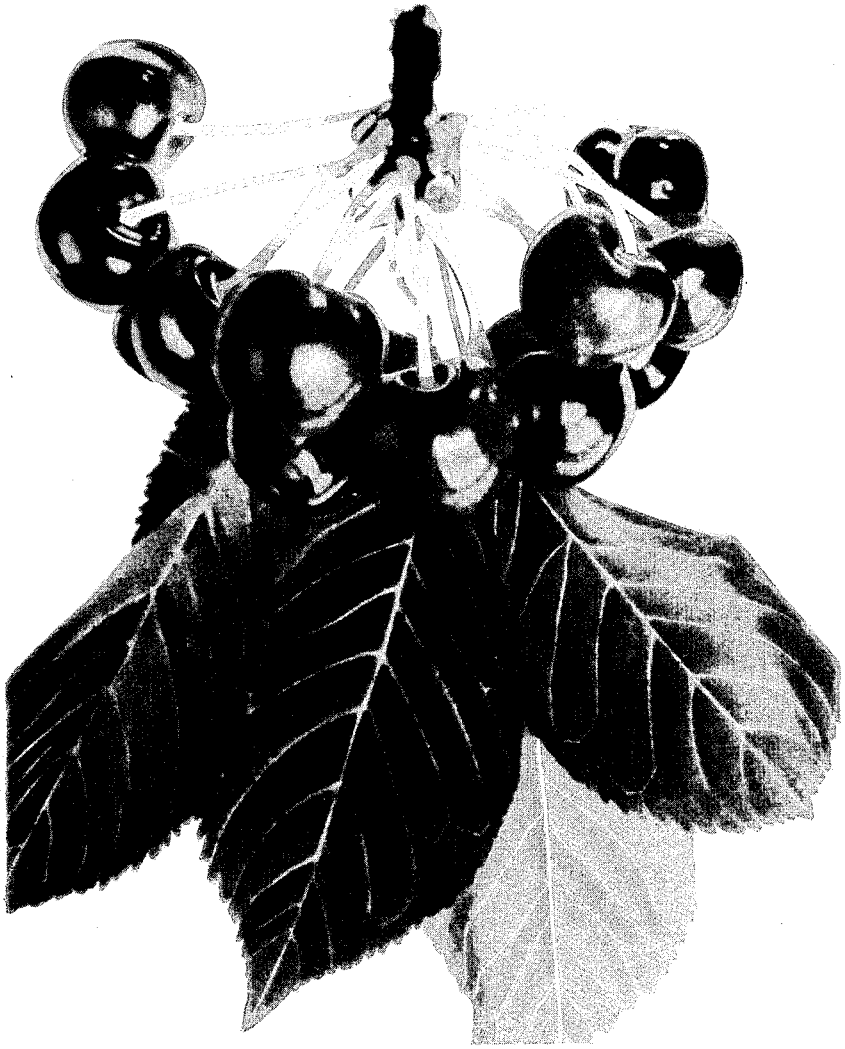
Inventor
O. R. Meyer
By Robbins & Robbins
attorneys Patented Oct. 7, 1947

Plant Pat. 764

UNITED STATES PATENT OFFICE

764

CHERRY TREE

Ottilie R. Meyer, Cedarburg, Wis., assignor to Stark Bro's Nurseries and Orchards Company, Louisiana, Mo., a corporation of Missouri Application April 18, 1946, Serial No. 663,086

1 Claim. (Cl. 47—62)

The present discovery relates to a new and distinct variety of cherry tree originating as a seedling, which has been developed and thoroughly tested by me on my property over a period of years to determine its fixed characteristics more particularly pointed out hereinafter.

This new variety is a sweet cherry and is extremely hardy, as demonstrated by the fact that it has survived and borne annual crops near Cedarburg, Wisconsin, where other varieties of sweet cherries have been winter-killed.

Another important characteristic is that this new cherry has produced and continues to produce regularly year after year, heavy crops. This variety of sweet cherry is of outstanding hardiness, productiveness, and reliability of bearing.

These characterisctics in combination with the unique color of the fruit, make this variety very desirable for commercial purposes and especially valuable in sections of this country where temperatures go as low as 30° below zero.

Asexual reproduction of this new variety shows the foregoing characteristics come true to form and are established.

The drawing shows a specimen cluster of the fruit showing the general coloring as nearly as possible to depict, and a typical group of leaves of this variety.

The following is a detailed description of the new variety, color terminology being in accord with Ridgeway's Color Standard, except where otherwise indicated to have ordinary dictionary significance:

The specimens described were grown at Louisiana, Missouri.

Dates first and last picking, June 12th–June 20th.

Tree: Large; vigorous; dense; upright; spreading; round topped; hardy; very productive; regular bearer.

*Trunk.*—Stocky medium smooth.

*Branches.*—Slender; Liver Brown, Plate XIV, color 7 tone. Lenticels—medium number; large.

*Leaves.* — Length — 4.7 inches. Width — 2 inches. Size—medium. Obovate-oblong; acutely pointed; medium thick. Color—Elm Green, Plate XVII, color 27′ tone. Smooth. Margin—finely serrate. Petiole — medium long; medium thick. Glands—average number 1 to 3, mostly 2; alternate for most part; large; reniform; free; glabrous.

Flowers: Date full blossom—May 2 (in 1944), with other sweet cherries. Medium late compared with other varieties. Medium size; white.

Fruit:

*Maturity when described.*—Eating ripe, June 16th. Matures with "Bing" and "Deacon."

*Size.*—Uniform; medium size. Axial diameter—.75 inch. Transverse in suture plane—.75 inch. At right angles to suture plane—.85 inch.

*Form.*—Uniform; unsymmetrical; broadly ovoid; sides equal; ventral surface compressed and slightly flattened. *Suture*—an inconspicuous line disappearing near base. *Ventral surface* — Rounded. *Cavity* — rounded; depth and breadth medium. Markings—none. *Base*—rounded. *Apex*—rounded with slightly depressed Russet dot pistil point. *Stem*—length, 1⅜ inches; slender; glabrous. Adherence to fruit, weak. *Skin*—medium thin; medium tender; astringency—relatively free of. Tendency to break—slight in wet season, none in dry season. Color—Nopal Red, Plate 1, color 3 tone i; ground color uniformly and heavily mottled with Maroon, Plate I, color 3 tone m. When dead ripe almost black with a tinge of red; very attractive combination. Dots—numerous; indistinct.

Flesh:

*Color.*—Light Ochraceous Salmon, Plate XV, color 13′ tone b, with Rose Doree, Plate I, color 3 tone b, near stone.

*Surface of pit cavity.*—Pomegranate Purple, Plate XII, color 71 tone i.

*Amygadalin.*—Moderate.

*Texture.*—Firm; meaty; breaking.

*Fibres.*—Few; fine; tender.

*Ripens.*—Fairly even.

*Flavor.*—Subacid; delicate; sweet.

*Aroma.*—Wanting.

*Eating quality.*—Excellent.

Stone: Semi-free to almost free; adheres to flesh along both dorsal and central edges.

*Fibres.*—Free.

*Size.*—Medium; ⅜ x ⅜ x ¼ inch.

*Form.*—Oval; obovoid compressed.

*Base.*—Straight; narrow; oblong.

*Sides.*—Equal; curved on left side.

*Surface.*—Regularly furrowed near ventral edge.

Use: Market; local; dessert; culinary; canning.

Keeping quality: Medium.

Resistance to: Insects—medium; diseases—medium.

Shipping quality: Medium.

I claim:

A new and distinct sweet variety of cherry tree characterized as to novelty by its extreme hardiness, its habit of producing heavy crops regularly year after year, and the coloring of its fruit, substantially as shown and described.

OTTILIE R. MEYER.